United States Patent [19]

Wachtel

[11] Patent Number: 4,840,189

[45] Date of Patent: Jun. 20, 1989

[54] RESTRAINING VEST

[76] Inventor: Roberta S. Wachtel, 10469 Puttygut Rd., Richmond, Mich. 48062

[21] Appl. No.: 150,151

[22] Filed: Jan. 29, 1988

[51] Int. Cl.[4] .............................................. A61F 13/00
[52] U.S. Cl. ...................................... 128/869; 128/874
[58] Field of Search ........................ 128/133, 134, 135; 297/465

[56] References Cited

U.S. PATENT DOCUMENTS

| | | | |
|---|---|---|---|
| 2,722,694 | 11/1955 | Bryant | 128/134 |
| 2,827,898 | 3/1958 | Thompson | 128/134 |
| 2,888,009 | 5/1959 | Taylor | 128/134 |
| 3,108,292 | 10/1963 | Bodnar et al. | 128/134 |
| 3,136,311 | 6/1964 | Lewis | 128/134 |
| 3,137,294 | 6/1964 | Robertson | 128/134 |
| 3,181,530 | 5/1965 | Storey | 128/134 |
| 3,191,599 | 6/1965 | Kendell | 128/134 |
| 3,236,234 | 2/1966 | Buckley | 128/134 |
| 3,265,065 | 8/1966 | Jillson | 128/134 |
| 3,407,807 | 10/1968 | Giberson | 128/134 |
| 3,788,309 | 1/1974 | Zeilman | 128/134 |
| 3,897,778 | 8/1975 | Forbes-Robinson et al. | 128/134 |
| 4,026,282 | 5/1977 | Thomas | 128/134 |
| 4,050,737 | 9/1977 | Jordan | 128/134 X |
| 4,119,095 | 10/1978 | Lewis | 128/134 |
| 4,132,230 | 1/1979 | Ladd | 128/134 |
| 4,360,014 | 11/1982 | Manahan | 128/134 |
| 4,515,155 | 5/1985 | Wagemann | 128/134 |
| 4,571,000 | 2/1986 | Holder | 128/134 X |
| 4,608,973 | 9/1986 | Green et al. | 128/134 |
| 4,653,131 | 3/1987 | Diehl | 5/494 |

FOREIGN PATENT DOCUMENTS 728849 4/1955 United Kingdom ............... 297/465

OTHER PUBLICATIONS

Catalog entitled "The Posey Inservice Guide", J. T. Posey Co., 5635 Peck Rd., Arcadia, Calif., 91006–0020, copyright 1983, pp. 24.

Catalog entitled "Patient Safety Aids", 1985 edition, J. T. Posey Company, 5635 Peck Rd., Arcadia, Calif., 91006–0020, pp. 35.

Primary Examiner—Robert A. Hafer
Assistant Examiner—Kevin G. Rooney
Attorney, Agent, or Firm—Harness, Dickey & Pierce

[57] ABSTRACT

A patient restraining vest having a main body panel comprising front and pack panel portions and a head opening. A pair of straps extending in opposite directions from the front panel portion is provided for wrapping around the patient to secure the patient in the vest. A third strap extending in both directions from the front panel portion is provided for wrapping around the frame of a supporting structure such as a bed, chair or the like, and attaching to each strap the pair of straps to restrain the patient to the supporting structure. An opening is provided to access to the patient's chest without removing the vest.

10 Claims, 2 Drawing Sheets

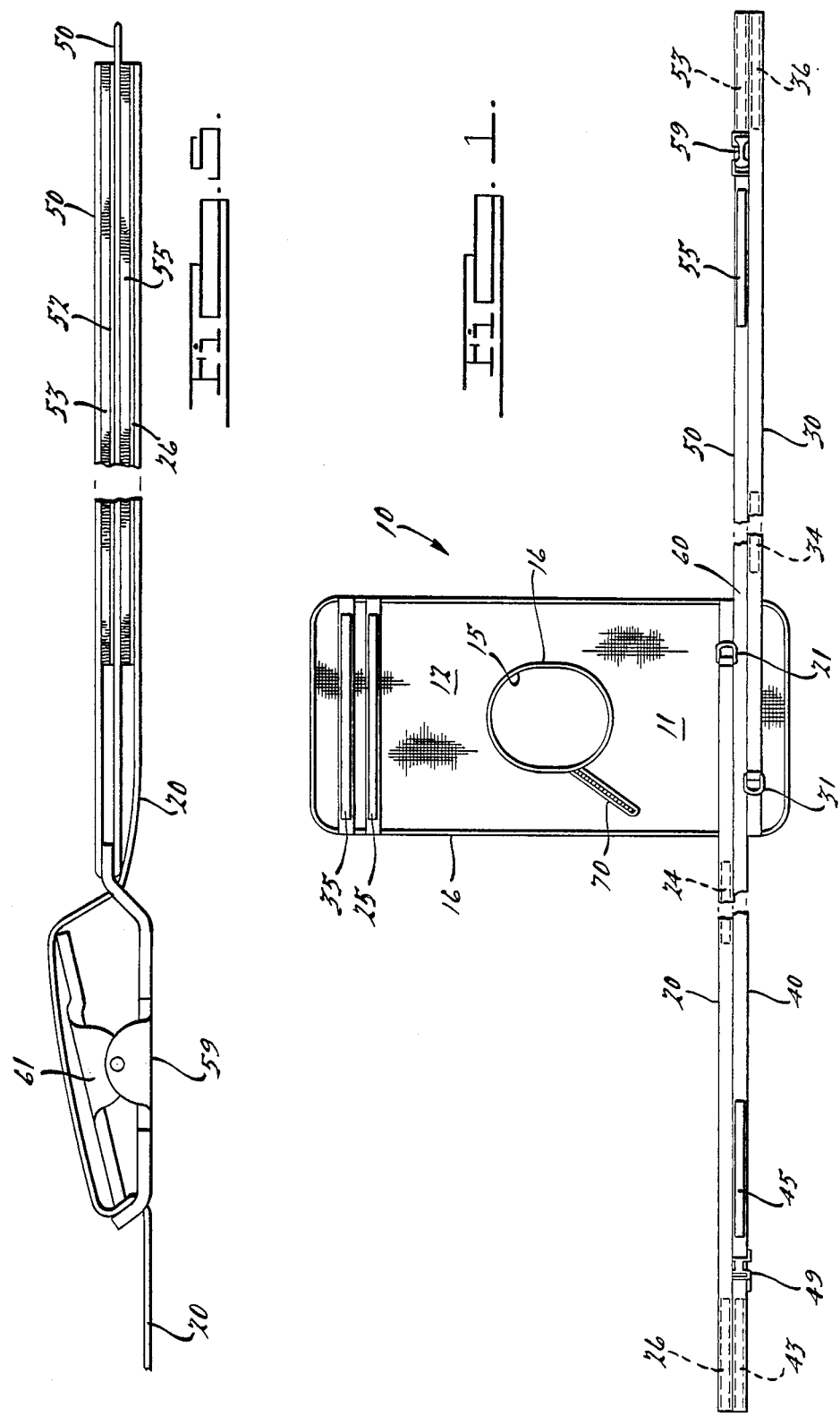

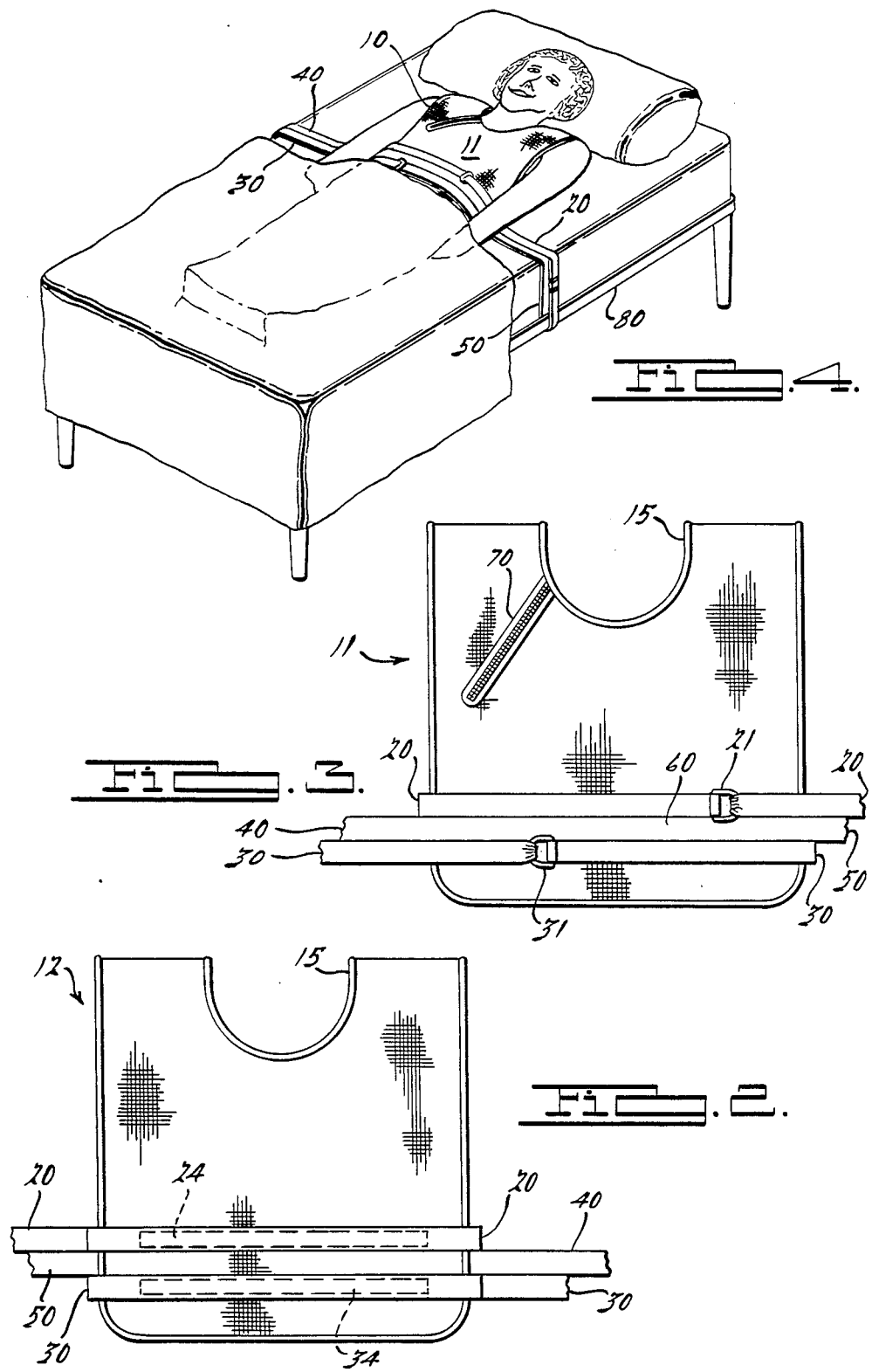

RESTRAINING VEST

BACKGROUND OF THE INVENTION

The present invention relates to a vest for restraining a patient in a supporting structure having a frame such as a bed, chair or the like, but allowing a limited degree of movement. Restraints of this type have a number of applications including restraining elderly people or surgical patients who could be injured while attempting to get out of bed on their own or restraining mentally ill patients to maintain control.

Patient restraining devices are well known in the art. These devices generally have one or more deficiencies including: difficulty in putting the device on the patient, such as arm holes to feed the patient's arm through; no means to secure the device on the patient separate from the means for securing the device to the bed, which can result in tightening of the device due to the movement of the patient; and difficulty in accessing the patient's chest while in the device to monitor various medical instruments such as a subclavian intravenous tube. Some examples of such devices are disclosed in the following patents: U.S. Pat. No. 3,137,294 to Robertson; U.S. Pat. No. 3,181,530 to Storey; and U.S. Pat. No. 3,265,065 to Jillson.

SUMMARY OF THE INVENTION

The present invention provides a patient restraining vest which is light-weight, durable and simple to use. The vest provides a limited amount of movement of the patient, but will not tighten around the patient's chest and abdomen as a result of the movement. Further, the vest provides access to the patient's chest without necessitating removal of the vest.

The present invention comprises a body portion formed of one piece of a synthetic mesh material having front and back panels and a centrally located opening for the patient's head and neck. The front panel of the vest has two straps extending from each side. One strap on each side is wrapped around the patient's back where it is attached to the back panel of the vest by means of a hook and loop fastener such as "Velcro". These straps continue to wrap around to the front panel whereby they each pass through a "D" ring and are then pulled to the patient's side. The "Velcro" fasteners provide adjustability to use one size vest on various size patients.

A spring clasp is attached to the end of the other strap extending from each side. The patient is restrained to the bed by routing the two straps on each side around the bed frame and attaching the straps together with the spring clasps. Because the vest is secured to the patient when the straps are wrapped around the patient and attached to the back panel, movement of the patient, once restrained to the bed, will not cause the vest to tighten on the patient.

"Velcro" fasteners are attached to the end of the straps so that the excess length of strap passed through the spring clasps can be tightly secured to the other strap. The spring clasps are detachable for ease in laundering of the vest.

Also included is a zippered opening at the right front of the neck opening to provide access to the patient's chest to monitor various medical instruments such as subclavian intravenous tube site.

Additional advantages and features of the present invention will become apparent from the subsequent description and the appended claims taken in conjunction with the accompanying drawings.

BRIEF DESCRIPTION OF THE DRAWINGS

FIG. 1 is a plan view of the vest in accordance with the present invention with the vest shown laying flat.

FIG. 2 is a back elevation view of the vest of FIG. 1.

FIG. 3 is a front elevation view of the vest of FIG. 1.

FIG. 4 is a perspective view illustrating the vest in use.

FIG. 5 is a side view of the spring clasp and straps forming a part of the vest shown in operative secured relationship.

DETAILED DESCRIPTION OF THE PREFERRED EMBODIMENT

Referring to FIG. 1, a restraining vest in accordance with the present invention is shown generally at 10 having a body panel laying flat comprised of a front panel portion 11 and a back panel portion 12. The body panel is preferably made of a synthetic mesh material which is light-weight, durable and easily laundered although other suitable materials may be used. The straps described below are preferably made of nylon although again other materials may be substituted therefor. Head and neck opening 15 is centrally located in body panel 10 for the patient's head and neck to extend through with the vest resting on the patient's shoulders. Front panel portion 11 covers the patient's chest and abdomen while the back panel portion 12 covers the patient's back. A bias tape trim 16 is sewn to the outer edge of the body panel and around neck opening 15. A first pair of straps, upper strap 20 and lower strap 30 extend laterally across and outwardly in opposite directions beyond the lateral side edges of front panel portion 11. A pair of "D" rings 21 and 31 are attached to straps 20 and 30 respectively. Ring 21 is attached near the left lateral side edge of front portion panel 11 while ring 31 is attached near the right lateral side edge of front panel portion 11 as shown in FIG. 1. Sewn to the back side of upper strap 20 in spaced relationship are two elongated portions 24 and 26 of a hook and loop-type fastener such as "Velcro". Both portions 24 and 26 are preferably the loop portion of such a fastener. Likewise, sewn to the back of lower strap 30 in spaced relationship are elongated loop portions 34 and 36 of a hook and loop fastener. Sewn laterally across the entire width of back panel portion 12 are two hook portions 25 and 35 of a "Velcro" fastener. Hook portions 25 and 35 are located approximately the same distance from the neck opening 15 as are straps 20 and 30 respectively.

The vest is placed on the patient by draping the vest over the patient's shoulders with the patient's head and neck extending through neck opening 15. Upper strap 20 is wrapped around the patient's right side and back with "Velcro" loop portion 24 engaging with hook portion 25 to fasten strap 20 to back panel portion 12. Upper strap 20 is continued around the patient's left side, routed through "D" ring 21 and pulled outward to the patient's left. Likewise, lower strap 30 is wrapped around the patient's left, across back panel portion 12 engaging "Velcro" fastener portions 34 and 35, around the patient's right side, through "D " ring 31 and pulled to the patient's right. Preferably, loop portions 24 and 34 will have a length equal to or greather than the length of hook portions 25 and 35 so as to insure a substantial length of engagement of the fastener portions while still allowing adjustment to accommodate patients of varying girth. The hook portions 25 and 35 used to attach straps 20 and 30 to back panel portion 12 extend the entire width across back panel portion 12. This length is provided to make it difficult for the patient, particularly while restrained in bed on his or her back, to remove straps 20 and 30 from the back panel portion 12. In order to remove the straps, the entire length of the "Velcro" fasteners must be disengaged at one time. Thus, it is difficult for patients to loosen the vest themselves.

FIG. 2 shows the back panel portion 12 with the upper and lower straps 20 and 30 respective wrapped around back panel portion 12 and the "Velcro" loop portions 24 and 34 (shown) engaged with "Velcro" hook portions 25 and 35 (not shown).

FIG. 3 shows the front panel portion 11 with upper and lower straps 20 and 30 respectively wrapped around the patient and routed through "d" rings 21 and 31 respectively. The "Velcro" fasteners on back panel portion 12 and straps 20 and 30 allow one size vest to be adjusted for use on various size patients. At this point, the patient is secured in the vest. The remainder of strap 20 now extends to the patient's left while strap 30 now extends to the patient's right. The "Velcro" fastener on back panel portion 12, in addition to preventing the patient from loosening the vest, also prevents the vest from being tightened on the patient by movement of the patient. The entire length of the "Velcro" fasteners must first be disengaged before straps 20 and 30 can be tightened around the patient. Movement of the patient will not cause tightening of the vest.

A middle strap 60 extends laterally across front panel portion 11 and outwardly in opposite directions beyond the lateral side edges of front panel portion 11. Middle strap 60 is shown with a first portion 40 extending pareallel to and below upper strap 20. A second portion 50 extends parallel to and above lower strap 30. Sewn to the front of first and second middle strap portions 40 and 50 are "Velcro" hook portions 45 and 55 respectively. Sewn onto the back of middle strap portions 40 and 50 are two "Velcro" fastener portions. Hook portion 43 and loop portion 42 (not shown) are sewn to the back of middle strap portion 40, while hook portion 53 and loop portion 52 (not shown) are sewn to the back of middle strap portion 50. Portions 42 and 52 are on the back of middle strap portions 40 and 50, opposite portions 45 and 55 respectively. Spring clasps 49 and 59 are attached to middle straps portions 40 and 50 respectively by routing the straps 40 and 50 through the mounting slot of clasps 49 and 59. The ends of middle strap portion 40 and 50 are folded over such that "Velcro" portions 43 and 42 engage and "Velcro" portions 53 and 52 engage as shown in FIG. 5 with middle strap portion 50. The "Velcro" attachment of clasps 49 and 59 allows the clasps to be removed during laundering of the vest.

The patient secured in the vest, is restrained in bed laying on his or her back, as shown in FIG. 4. Middle strap portion 50 and upper strap 20 are wrapped around the left side of bed frame 80. Upper strap 20 is attached to middle strap 50 by spring clasp 59 as shown in FIG. 5. Upper strap 20 is fed through the clasp portion of spring clasp 59 until the upper strap 20 and middle strap portion 50 are pulled to the desired position around bed frame 80 to restrain the patient. Upper strap 20 is then fed through the other end of clasp 59 and "Velcro" portions 26 and 55 are engaged to retain the excess length of strap 20 to middle strap portion 50 as shown in FIG. 5. Overlaying strap 20 on the release portion 61 of spring clasp 59, increases the difficulty for a patient to release himself from the bed. Before the strap 20 can be released from the spring clasp 59, the "Velcro" portions 26 and 55 must be completely disengaged and strap 20 pulled back through spring clasp 59. This is difficult for a restrained patient who will generally not be able to reach the straps or spring clasp. This same procedure is repeated with lower 30 and middle strap portion 40 on the patient's right side to secure the patient to the right side of bed frame 80 with "Velcro" portions 36 and 45 being engaged.

Zipper opening 70 is provided at neck opening 15 extending radially from opening 15 on the right side of front panel portion 11 to provide access to the patient's chest without removing the restraint as may be needed for monitoring various medical instruments such as a subclavian intravenous tube.

This arrangement of straps allows for ease in securing the patient in the vest. The straps can be easily wrapped around the patient avoiding the difficulty of having to move the patient's arms through arm holes as required with some prior restraint designs. Additionally, once the straps 20 and 30 are wrapped around the patient, the patient is secured in the vest. The vest, with the patient secured therein, is then attached to the bed frame 80. This allows limited patient movement in bed without causing the vest to tighten around the patient's chest and abdomen. Such tightening can cause the patient to panic or inhibit breathing or blood circulation. Furthermore, once restrained, the patient is unable to loosen the restraint and get out of bed by himself. To loosen the vest, the patient must separate lower 30 and upper 20 straps from the back panel portion 12. This would require separating the entire length of "Velcro" across back panel portion. This vest also provides access to the patient's chest.

It is understood that the invention is not limited to the exact construction illustrated and described above, but that various changes and modifications may be made without departing from the spirit and scope of the invention as defined in the following claims.

I claim:

1. A vest for restraining a patient in a supporting structure, said supporting structure having a frame, comprising:

a main body including a front panel portion, a back panel portion and a centrally located opening for receiving a patient's head and neck;

a pair of straps extending laterally in opposite directions beyond the lateral side edges of said front panel portion, said pair of straps being of sufficient length to extend around the back of said patient;

a first means for releasably fastening said pair of straps to said back panel portion;

a pair of means for guiding each strap of said pair of straps after said first straps are extended around said patient's back and fastened to said back panel portion, said guide means attached to said front panel portion;

a third strap extending laterally in opposite directions beyond both lateral side edges of said front panel portion, said third strap for routing around said frame of said supporting structure;

a second means for fastening said pair of straps to said third strap whereby a patient wearing said vest may be restrained in said supporting structure.

2. A vest for restraining a patient, as set forth in claim 1, further comprising:
   a means for accessing said patient's chest beneath said vest without removing said vest.

3. A vest for restraining a patient, as set forth in claim 1 wherein:
   said first fastening means comprises a hook and loop fastener.

4. A vest for restraining a patient, as set forth in claim 1 wherein:
   said second fastening means comprises a spring clasp attached to each end of said third strap.

5. A vest for restraining a patient, as set forth in claim 4, wherein:
   said spring clasps are removably attached to said third strap.

6. A vest for restraining a patient, as set forth in claim 2, wherein:
   said access means comprises a zipper opening extending radially from said head and neck opening on the right side of said front panel portion.

7. A vest for restraining a patient in a supporting structure, said supporting structure having a frame, comprising:
   a main body panel including a front panel portion and a back panel portion and a centrally located opening for receiving a patient's head and neck;
   an upper strap laterally crossing said front panel portion extending beyond one lateral side edge of said front panel portion, said upper strap having two releasable fasteners attached to the back side thereof;
   a means for guiding said upper strap attached to said upper strap near the opposite lateral side edge from which said upper strap extends;
   a lower strap laterally crossing said front panel portion extending beyond the opposite lateral side edge of said front panel portion from which said upper strap extends, said lower strap having two releasable fasteners attached to the back side thereof;
   a means for guiding said lower strap attached to said lower strap near the opposite lateral side edge from which said lower strap extends;
   a middle strap extending laterally in opposite directions beyond both lateral side edges of said front panel portion;
   means, removably mounted to each end of said middle strap, for releasably attaching each strap of said pair of straps to said middle strap;
   a releasable fastener attached to the front side of each end of said middle strap adjacent to said attaching means;
   two releasable fasteners laterally attached to said back panel portion at a distance from said head and neck opening approximately equal to the distance from said head and neck opening to said upper and lower straps respectively.

8. A vest for restraining a patient, as set forth in claim 7, further comprising:
   a zipper opening extending radially from said head and neck opening on the right side of said front panel portion.

9. A vest for restraining a patient in a bed having a frame, comprising:
   a main body panel including a front panel portion and a back panel portion and a centrally located opening for receiving a patient's head and neck;
   an upper strap laterally crossing said front panel portion extending beyond the right lateral side edge of said front panel portion, said upper strap having a 'D' ring attached thereto near the left edge of said front panel portion and two loop portions of a hook and loop fastener attached to the back side of said upper strap;
   a lower strap laterally crossing said front panel portion extending beyond the left lateral side edge of said front panel portion, said lower strap having a "D" ring attached thereto near the right edge of said front panel portion and two loop portions of a hook and loop fastener attached to the back side of said lower strap;
   a middle strap extending beyond both the left and right lateral side edges of said front panel portion;
   a spring clasp removably attached to each end of said middle strap by a hook and loop fastener;
   a loop portion of a hook and loop fastener attached to the front side of each end of said middle strap adjacent to said spring clasps;
   two hook portions of a hook and loop fastener laterally attached to said back panel portion, at a distance from said head and neck opening approximately equal to the distance from said head and neck opening to said upper and lower straps respectively.

10. A vest for restraining a patient, as set forth in claim 9, further comprising:
    a zipper opening extending radially from said head and neck opening on the right side of said front panel portion.

* * * * *